United States Patent
Hytonen et al.

(10) Patent No.: US 11,253,214 B2
(45) Date of Patent: Feb. 22, 2022

(54) STATISTICAL METHOD FOR MATERIAL PROPERTY EXTRACTION FROM MULTI-ENERGY IMAGES

(71) Applicant: Varian Medical Systems International AG, Cham (CH)

(72) Inventors: Roni Hytonen, Cham (CH); Timo K. Koponen, Cham (CH); Perttu Niemela, Cham (CH)

(73) Assignee: Varian Medical Systems International AG

( * ) Notice: Subject to any disclaimer, the term of this patent is extended or adjusted under 35 U.S.C. 154(b) by 52 days.

(21) Appl. No.: 16/713,963

(22) Filed: Dec. 13, 2019

(65) Prior Publication Data
US 2021/0177366 A1 Jun. 17, 2021

(51) Int. Cl.
*A61B 6/00* (2006.01)
*G06T 11/00* (2006.01)
*G06T 7/174* (2017.01)

(52) U.S. Cl.
CPC .......... *A61B 6/482* (2013.01); *A61B 6/4241* (2013.01); *A61B 6/5247* (2013.01); *A61B 6/585* (2013.01); *G06T 7/174* (2017.01); *G06T 11/008* (2013.01)

(58) Field of Classification Search
CPC .............................. G06T 11/008; G06T 7/174
See application file for complete search history.

(56) References Cited

U.S. PATENT DOCUMENTS

| | | | |
|---|---|---|---|
| 2007/0040831 A1* | 2/2007 | Flohr | G06T 5/20 345/424 |
| 2008/0253508 A1* | 10/2008 | Krauss | A61B 6/032 378/19 |
| 2009/0086884 A1* | 4/2009 | Krauss | A61B 6/481 378/5 |
| 2017/0086769 A1* | 3/2017 | Allmendinger | A61B 6/5205 |
| 2017/0294042 A1* | 10/2017 | Engel | G06T 15/506 |
| 2018/0113227 A1* | 4/2018 | Lin | G01T 7/005 |
| 2019/0317231 A1* | 10/2019 | Hofmann | A61B 6/032 |

* cited by examiner

*Primary Examiner* — Michael C Bryant
(74) *Attorney, Agent, or Firm* — Vista IP Law Group, LLP

(57) ABSTRACT

An apparatus for determining material property, includes: an interface configured to obtain a first HU value associated with a first image of an object, and to obtain a second HU value associated with a second image of the object, wherein the first image is created using a first energy having a first energy level, and wherein the second image is created using a second energy having a second energy level that is different from the first energy level; and a processing unit configured to determine a weighted property value for the object based at least in part on the first HU value and the second HU value.

17 Claims, 10 Drawing Sheets

1000

1002 obtaining, by an interface of the apparatus, a first HU value associated with a first image of an object, and to obtain a second HU value associated with a second image of the object, wherein the first image is created using a first energy having a first energy level, and wherein the second image is created using a second energy having a second energy level that is different from the first energy level

1004 determining, by a processing unit of the apparatus, a weighted property value for the object based at least in part on the first HU value and the second HU value

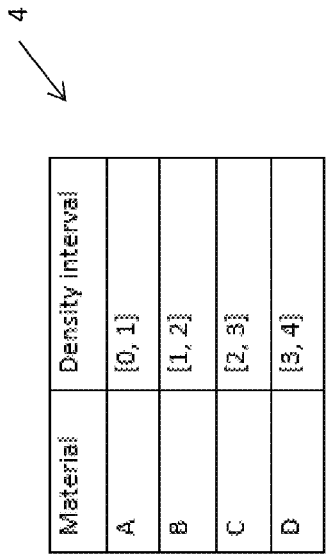
FIG. 1
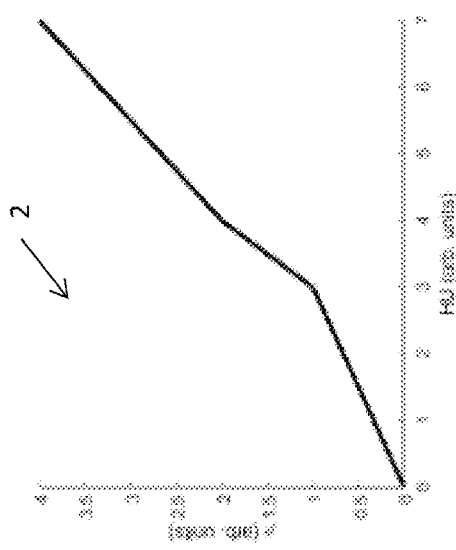
FIG. 2A
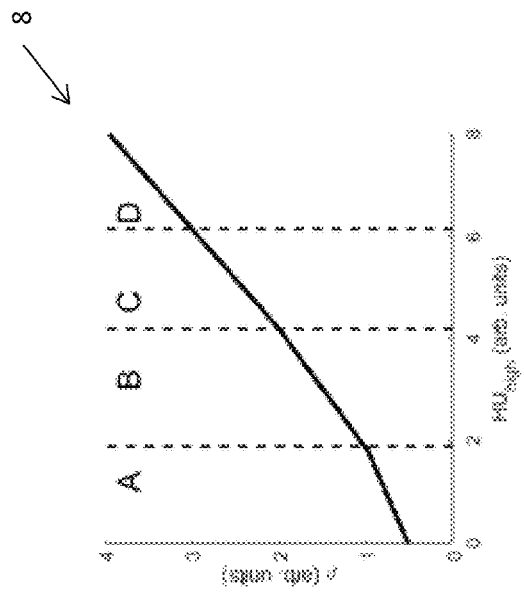
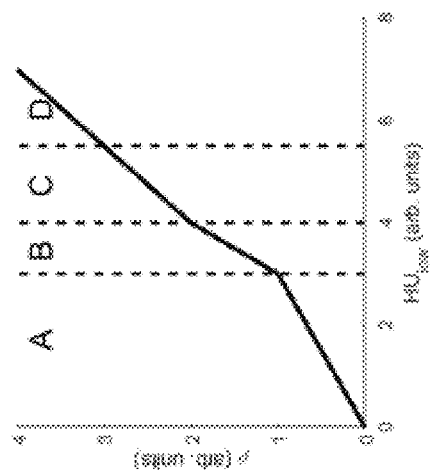
FIG. 2B

| Material | Density Range [min, max] | HU$_{Low}$ Range [min, max] | HU$_{High}$ Range [min, max] |
|---|---|---|---|
| A | [0.3, 0.7] | [0.60, 1.33] | [0.66, 1.23] |
| B | [0.6, 1.0] | [1.17, 1.57] | [1.17, 1.57] |
| C | [0.9, 1.3] | [1.53, 1.80] | [1.43, 1.85] |
| D | [1.4, 1.7] | [1.90, 2.20] | [1.93, 2.13] |

FIG. 7

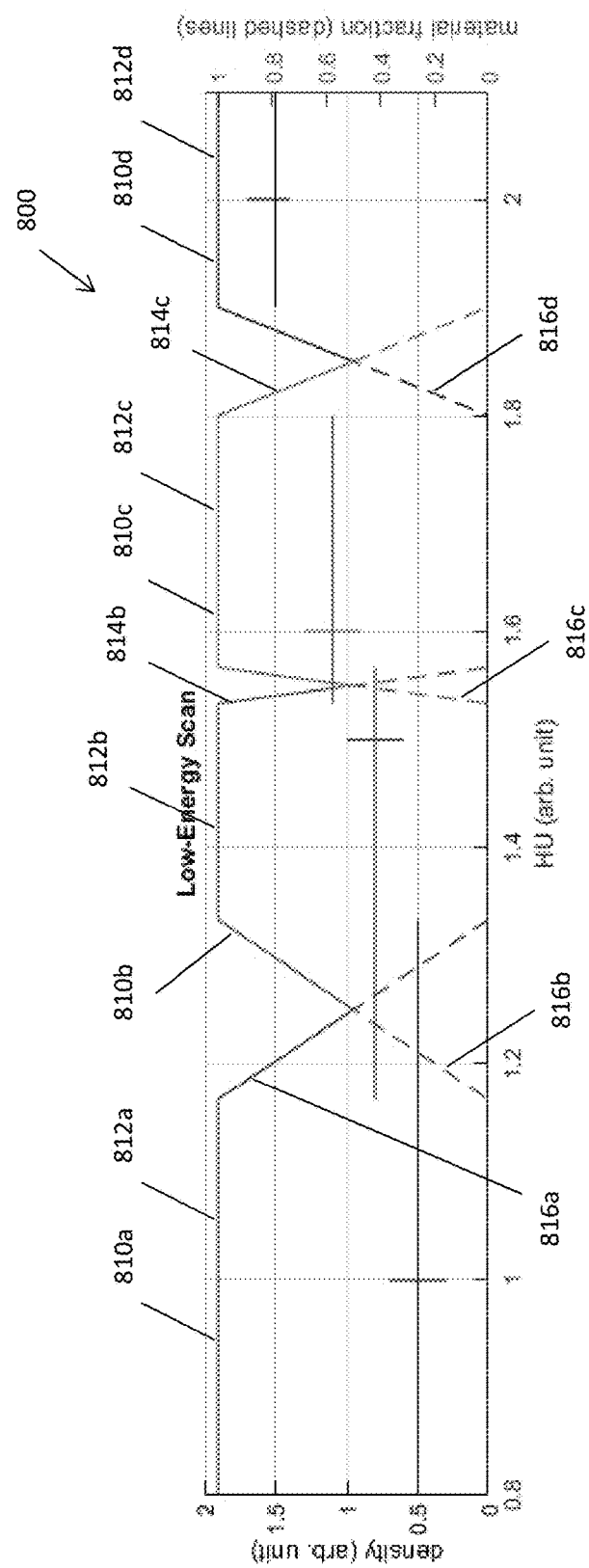
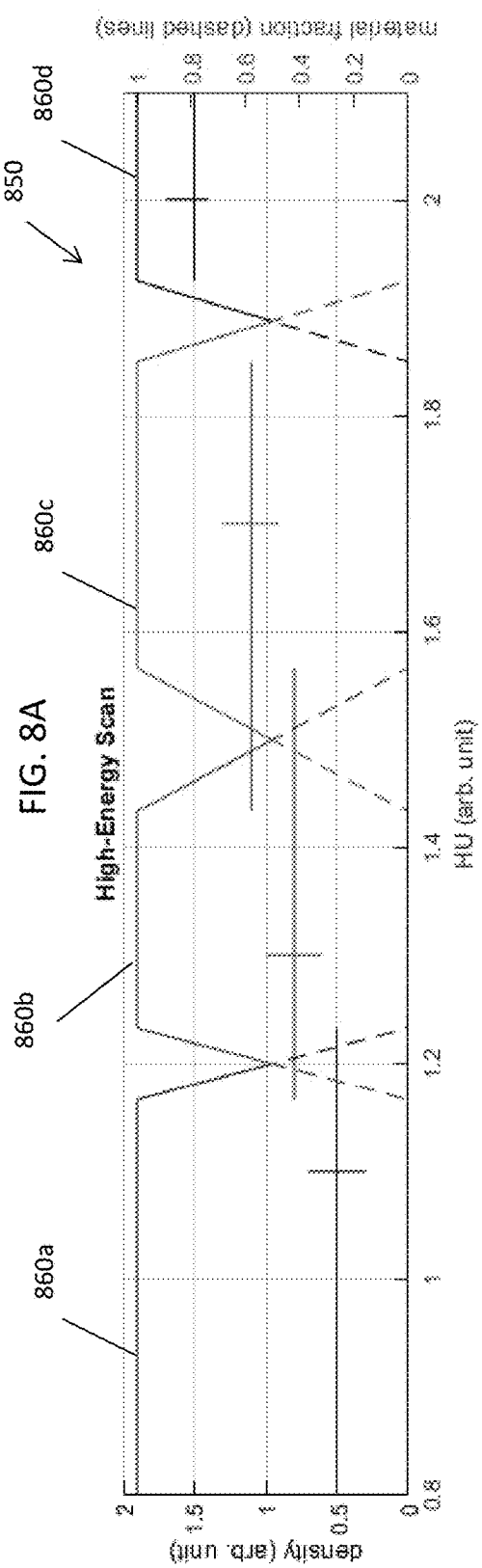
FIG. 8A
FIG. 8B

STATISTICAL METHOD FOR MATERIAL PROPERTY EXTRACTION FROM MULTI-ENERGY IMAGES

FIELD

The field of the application relates to imaging for determining material property, and more particularly, to systems and methods for determining material property based on multi-energy images.

BACKGROUND

Single-Energy Computed Tomography (SECT) is currently the cornerstone of radiation treatment planning, but it has a significant shortcoming of not being able to differentiate between certain materials. The result of a CT scan is an image of the target, where each volume pixel (voxel) represents a small part of the target volume, and the physical properties (e.g. density, proton stopping power, electron density) of the target can be inferred from these voxel values (expressed in units HU). The problem, however, is that two materials with significantly different physical properties may appear similar in the single energy CT image, making it near-impossible to reliably extract the material properties from such image.

SUMMARY

Multi-Energy Computed Tomography (MECT) may be used to alleviate the shortcoming of SECT. How materials appear in a CT scan depends on the scanning energy and the material in question. Even if two different materials appear similar when scanned using one energy, it is possible that they exhibit differences when the scanning energy is changed. In addition to the determination of the physical properties of materials, techniques for enhancing the differentiation of materials (i.e. being able to tell which one or two materials have contributed to form the HU-value in a voxel) are described herein.

The techniques for determining material properties based on multi-energy imaging described herein would benefit radiation treatment planning. Radiation treatment planning relies on converting the results of a single-energy CT scan into the material properties using calibration curves. Embodiments of the technique for determining material properties described herein utilize this approach for any number of scanning energies, while augmenting it with straight-forward statistical analysis on the materials of interest. The end-result is an intuitive workflow that improves on the accuracy of material identification and treatment planning.

An apparatus for determining material property, includes: an interface configured to obtain a first HU value associated with a first image of an object, and to obtain a second HU value associated with a second image of the object, wherein the first image is created using a first energy having a first energy level, and wherein the second image is created using a second energy having a second energy level that is different from the first energy level; and a processing unit configured to determine a weighted property value for the object based at least in part on the first HU value and the second HU value.

Optionally, the weighted property value comprises a weighted density for the object.

Optionally, the weighted density is based on N weights calculated using N metric values for N respective imaging energies.

Optionally, the N metric values comprises a first metric value that indicates how well the first HU value correlates with a first property identification, and a second metric value that indicates how well the second HU value correlates with a second property identification.

Optionally, the N metric values are $M_1$-$M_N$, and the N weights are $W_1$-$W_N$ calculated as $W_n = M_n/(\text{Sum}(M_1\text{-}M_N))$, for n=1 to N.

Optionally, at least one of the N metric values is a goodness metric calculated from calibration error for a histogram of HU-value spread of a calibration sample.

Optionally, the processing unit is configured to determine an identity of the object based on the weighted property value.

Optionally, the processing unit is also configured to determine a first material fraction based on the first HU value, and a second material fraction based on the second HU value; and wherein the processing unit is configured to compute a metric for the object based on the first material fraction and the second material fraction.

Optionally, the metric indicates a percentage or an amount of an identified material in the object.

Optionally, the processing unit is configured to determine the first material fraction by accessing a non-transitory medium storing material fraction values as a function of HU values, or storing parameter(s) of function(s) associating the material fraction values with HU values.

Optionally, the apparatus further includes the non-transitory medium.

Optionally, the processing unit is configured to compute the metric for the object based on the first material fraction and the second material fraction, and also based on a first weight and a second weight.

Optionally, the metric is based on the first weight times the first material fraction and the second weight times the second material fraction.

Optionally, each of the first weight and the second weight is based at least on a first metric value and a second metric value.

Optionally, the first weight is calculated as the first metric value divided by a sum of metric values that includes the first metric value and the second metric value; and wherein the second weight is calculated as the second metric value divided by the sum of metric values that includes the first metric value and the second metric value.

Optionally, the first metric value is a goodness metric calculated from calibration error for histogram of HU-value spread of a calibration sample.

Optionally, each of the first image and the second image comprises a CT image or a x-ray image.

Optionally, the apparatus further includes an imaging device configured to generate the first image and the second image, wherein the imaging device is a part of a medical device or a part of an object scanner.

A method performed by an apparatus, includes: obtaining, by an interface of the apparatus, a first HU value associated with a first image of an object, and to obtain a second HU value associated with a second image of the object, wherein the first image is created using a first energy having a first energy level, and wherein the second image is created using a second energy having a second energy level that is different from the first energy level; and determining, by a processing unit of the apparatus, a weighted property value for the object based at least in part on the first HU value and the second HU value.

Optionally, the weighted property value comprises a weighted density for the object.

Optionally, the weighted density is based on N weights calculated using N metric values for N respective imaging energies.

Optionally, the N metric values comprises a first metric value indicates how well the first HU value correlates with a first property identification, and a second metric value indicates how well the second HU value correlates with a second property identification.

Optionally, the N metric values are $M_1$-$M_N$, and the N weights are $W_1$-$W_N$ calculated as $W_n = M_n / (\text{Sum } (M_1\text{-}M_N))$, for n=1 to N.

Optionally, at least one of the N metric values is a goodness metric calculated from calibration error for histogram of HU-value spread of a calibration sample.

Optionally, the method further includes comprising determining, by the processing unit, an identity of the object based on the weighted property value.

Optionally, the method further includes determining, by the processing unit, a first material fraction based on the first HU value, and a second material fraction based on the second HU value; and computing, by the processing unit, a metric for the object based on the first material fraction and the second material fraction.

Optionally, the metric indicates a percentage or an amount of an identified material in the object.

Optionally, the first material fraction is determined by the processing unit accessing a non-transitory medium storing material fraction values as a function of HU values, or storing parameter(s) of function(s) associating the material fraction values with HU values.

Optionally, the metric for the object is computed based on the first material fraction and the second material fraction, and also based on a first weight and a second weight.

Optionally, the metric is based on the first weight times the first material fraction and the second weight times the second material fraction.

Optionally, each of the first weight and the second weight is based at least on a first metric value and a second metric value.

Optionally, the first weight is calculated as the first metric value divided by a sum of metric values that includes the first metric value and the second metric value; and wherein the second weight is calculated as the second metric value divided by the sum of metric values that includes the first metric value and the second metric value.

Optionally, the first metric value is a goodness metric calculated from calibration error for histogram of HU-value spread of a calibration sample.

Optionally, each of the first image and the second image comprises a CT image or a x-ray image.

Optionally, the method further includes generating the first image and the second image by an imaging device, wherein the imaging device is a part of a medical device or a part of an object scanner.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

FIG. 1 illustrates a graph for determining mass densities based on HU values, and a table for determining material based on density interval.

FIG. 2A illustrates material differentiation in HU space for imaging performed at first energy.

FIG. 2B illustrates material differentiation in HU space for imaging performed at second energy.

FIG. 7 illustrates a table listing examples of materials and their corresponding density ranges, HU ranges for low energy scan, and HU ranges for high energy scan.

FIG. 8A illustrates examples of density ranges and material fraction values for different materials as function of HU values for a low energy scan.

FIG. 8B illustrates examples of density ranges and material fraction values for different materials as function of HU values for a high energy scan.

DETAILED DESCRIPTION

Figure 3:
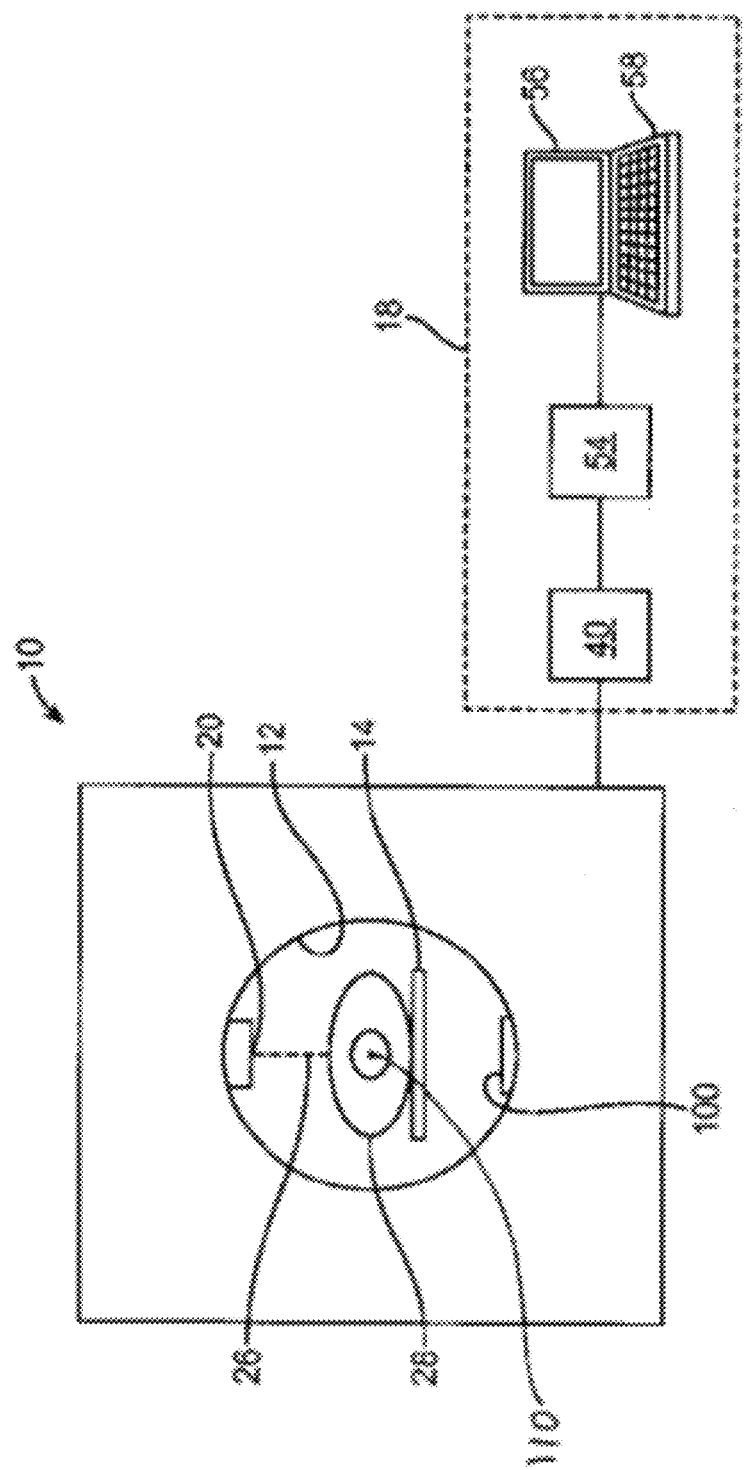
FIG. 3 illustrates a radiation system in accordance with some embodiments.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a technique of identifying a material. In particular, the figure illustrates a graph 2 for determining mass densities based on Hounsfield Units (HU) values, and a table 4 for determining material based on density interval.

HU are a dimensionless unit used in computed tomography (CT) scanning to express CT numbers in a standardized form. To use the graph 2 and the table 4, an imaging device is first used to image an object (e.g., patient, cargo, etc.) being examined. HU value(s) is then obtained from the imaging, and a mass density of the object being examined is then determined using the graph 2. For example, if a HU value from the imaging of the object is 3.5, then from the graph 2, it can be seen that the corresponding density is 1.5 for the object. Once the density of 1.5 is determined, the table 4 can then be used to identify the material composed in the object. As shown in the table 4, for density to be within the interval [1, 2], the material is material B.

In some cases, the table 4 for determining material based on density interval may be incorporated into the graph (i.e., the HU space), so that the graph 2 itself can be used to directly identify the material based on the HU value(s) in the imaging. For example, as shown in FIG. 2A, the material differentiation based on density intervals shown in the table 4 of FIG. 1 is incorporated into the graph 2 of FIG. 1 to form graph 6. Using the above example, for HU value of 3.5, it can be seen that the material is material B because the value of 3.5 is between the dotted lines marking HU=3 and HU=4 (which correspond with the density values of 1 and 2, respectively).

In the example of FIG. 2A, the graph 6 may be created based on imaging performed at a first energy. In some cases, there may be additional graph(s) created based on imaging performed at other energies. For example, as shown in FIG. 2B, a graph 8, which is similar to the graph 6, may be created based on imaging performed at a second energy that is different from the first energy associated with the graph 6. In some embodiments, the first energy may be lower than the second energy. Accordingly, in such cases, the first graph 6 may be a low energy graph, and the second graph 8 may be a high energy graph. In some cases, both graphs 6, 8 may be utilized in identifying a material of an object being examined. For example, the object may be imaged using first energy, and HU value from the resulting imaging may be 3.5. Then the object may be imaged again using second energy, and HU value from the resulting imaging may be 2.2. From the graph 6 of FIG. 2A, it can be seen that for HU=3.5 in first energy imaging, the material is identified as material B. From the graph 8 of FIG. 2B, it can be seen that for HU=2.2 in second energy imaging, the material is identified as material B as well. Accordingly, both energy scans confirm that the object being examined contains material B.

Embodiments of devices and methods are described herein for determining material properties and for identifying materials utilizing the above multi-energy imaging concept.

FIG. 3 illustrates a radiation system 10 configured to perform imaging at multiple different energies. The system 10 includes a gantry 12, a patient support 14 for supporting a patient 28, and a control system 18 for controlling an operation of the gantry 12. The system 10 also includes a radiation source 20 that projects a beam 26 of radiation towards the patient 28 while the patient 28 is supported on support 14, and an imager 100 located at an operative position relative to the source 20 (e.g., under the support 14). The radiation source 20 can be configured to generate a cone beam (e.g., as for CBCT), a fan beam, or other types of radiation beams in different embodiments.

In the illustrated embodiments, the radiation source 20 is an imaging radiation source for providing imaging energy. In such cases, the imager 100 is configured to receive imaging radiation and generate image signals in response thereto. The radiation source 20 is configured to provide imaging energy at different energy levels, e.g., two different energy levels, three different energy levels, etc.

In other embodiments, in addition to being an imaging radiation source, the radiation source 20 is also a treatment radiation source for providing treatment energy. In such cases, the imager 100 is configured to selectively receive imaging radiation or treatment radiation and generate image signals in response thereto.

In some embodiments, the treatment energy is generally those energies of 160 kilo-electron-volts (keV) or greater, and more typically 1 mega-electron-volts (MeV) or greater, and imaging energy is generally those energies below the high energy range, and more typically below 160 keV. In other embodiments, the treatment energy and the imaging energy can have other energy levels, and refer to energies that are used for treatment and imaging purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In the illustrated embodiments, the radiation source 20 is coupled to a ring gantry and is located within a bore. In other embodiments, the radiation source 20 may be coupled to an arm gantry.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during an imaging and/or a treatment procedure, the gantry 12 rotates about the patient 28 (as in a CT procedure and/or an arc-therapy). In other embodiments, the gantry 12 does not rotate about the patient 28 during a procedure. In such case, the gantry 12 may be fixed, and the patient support 14 is rotatable. The operation of the radiation source 20 and the gantry 12 (if the gantry 12 is rotatable) are controlled by the control 40, which provides power and timing signals to the radiation source 20, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the example described above, and that the system 10 may have other configurations in other embodiments. For example, in other embodiments, the system 10 may have different shapes. In other embodiments, the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. In still further embodiments, the system 10 may be any imaging system that has imaging capability.

In addition, in other embodiments, the radiation source 20 and/or the imager 100 may not be mounted on a ring gantry or an arm gantry. Instead, in other embodiments, the radiation source 20 and/or the imager 100 may be moveably or fixedly mounted to a structure in a room, such as to the floor of the room, the ceiling of the room, a beam in the room, a wall in the room, a frame in the room, or any combination of the foregoing. In further embodiments, the radiation source 20 and/or the imager 100 may be mounted on one or more robotic arms. In the case of the radiation source 20 and/or the imager 100 being moveably mounted to the structure in a room, the movement of the radiation source 20 and/or the imager 100 may be achieved manually or mechanically by a machine (e.g., motor). In further embodiments, the radiation source 20 and the imager 100 may be implemented on a hand-held device that allows a user to free carry and to move the radiation source 20 and the imager 100 to different positions and orientations for scanning different objects.

Furthermore, in other embodiments, instead of having the moveable radiation source 20 and the moveable imager 100, the system 10 may have a static radiation source and a static imager that remain stationary during use of the system 10 (e.g., during an imaging session).

In still further embodiments, the system 10 may have multiple radiation sources (e.g., x-ray sources), that cooperate with one imager 100 or with multiple imagers to generate images or detection data. In some embodiments, the multiple radiation sources and imager(s) may be mounted on the same ring or gantry. In other embodiments, the multiple radiation sources and imager(s) may be mounted to one or more structures in a room. In further embodiments, the multiple radiation sources and/or imagers may be sequentially arranged, as in the case of cargo scanning.

Also, in other embodiments, the system 10 may be an object inspection system. For example, in other embodiments, the system 10 may be configured to inspect cargo in an airport security department, to scan objects in a mail handling department, to scan objects in a security area, etc.

In the illustrated embodiments, the system 10 is configured to obtain images of an object (e.g., patient, cargo, etc.) being inspected, and determine one or more material properties, such as a density, for the object. In some embodiments, the system 10 is configured to determine material properties based on information in histograms generated for different calibration materials in different imaging energies, and/or based on information derived from such histograms. The histograms (or information in the histograms) and/or information derived from the histograms may be stored in a non-transitory medium. During use, the processing unit 54 of the system 10 may access such histograms information and/or information derived from the histograms for determining one or more material properties for object(s) being inspected or examined.

Figure 4A:
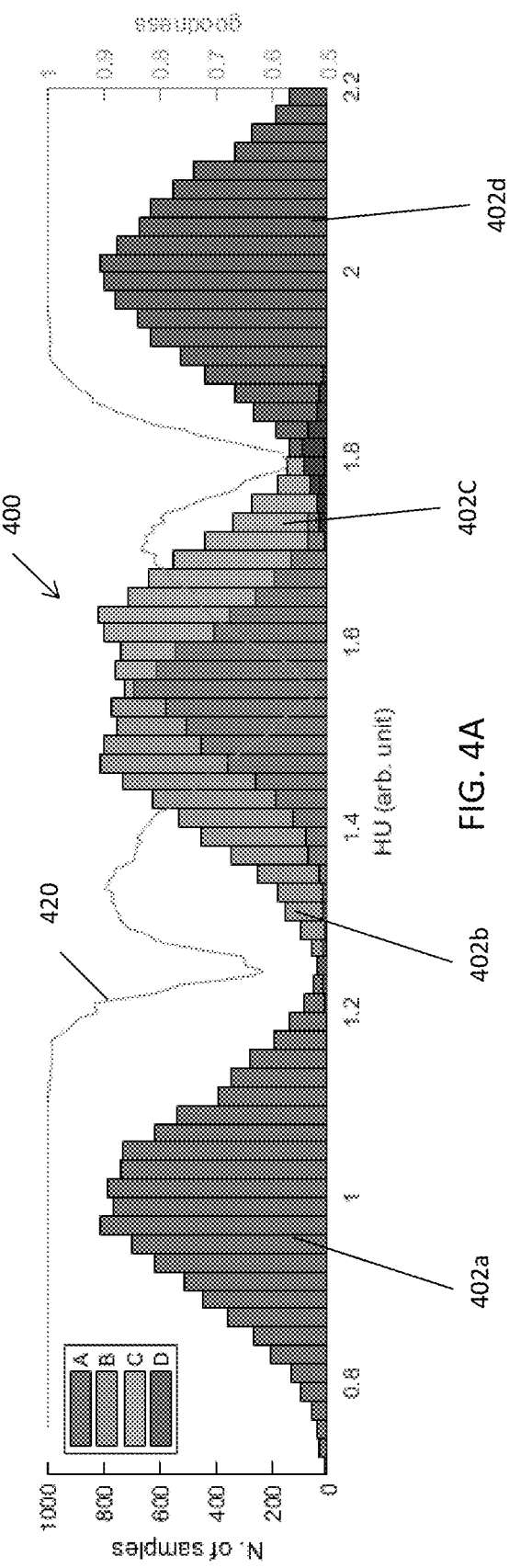
FIG. 4A illustrates a histogram of HU-value spread of several calibration samples obtained using a first energy scan, and a goodness metric calculated from calibration error.

FIG. 4A illustrates a histogram 400 of HU-value spreads of several calibration samples obtained using a first energy scan, and a goodness metric calculated from calibration error. In the illustrated example, the histogram 400 includes HU-value spreads of four samples (materials)—i.e., spreads 402a-402d for materials A, B, C, D, respectively. The materials A, B, C, D have known respective density values. The histogram 400 is generated using a first energy scan, and includes spreads of HU values for different calibration materials. As shown in the figure, the spread 402a for material A has a peak value when HU value is 1.0, the spread 402b for material B has a peak value when HU value is 1.5, the spread 402c for material C has a peak value when HU value is 1.6, and the spread 402d for material D has a peak value when HU value is 2.0. Accordingly, a calibration curve may be determined based on (HU, density) of the four materials A, B, C, D.

Figure 4B:
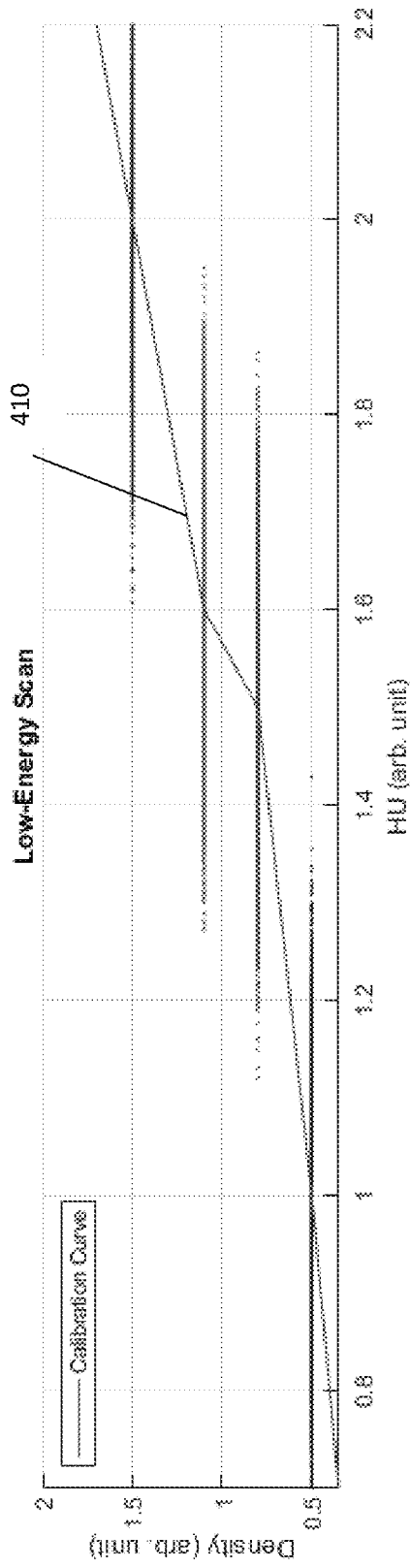
FIG. 4B illustrates a fitted calibration curve for the histogram of FIG. 4A.

FIG. 4B illustrates a fitted calibration curve 410 for the histogram 400 of FIG. 4A generated using the first energy. In particular, material A has known density value of 0.5, and it has a corresponding HU peak at HU=1.0. Material B has known density value of 0.8, and it has a corresponding HU peak at HU=1.5. Material C has known density value of 1.1, and it has a corresponding HU peak at HU=1.6. Material D has known density value of 1.5, and it has a corresponding HU peak at HU=2.0. These four points form part of the calibration curve 410 in FIG. 4B. The calibration curve 410 may be a line fitted to the measurements using any fitting methods, such as the least-squares method. In some embodiments, the calibration curve 410 may be determined as a piecewise linear least-squares fit to the data. In some cases, the calibration curve 410 may include line segments that connect the (HU, density) points for the different materials. The calibration curve 410 may be used to convert measured HU values of a sample into its density based on properties of the calibration materials (e.g., materials A, B, C, D). As shown in the figure, the spreads 402a-402d for the respective materials A, B, C, D are also superimposed onto the calibration curve 410.

As shown in FIG. 4A, a goodness metric represented by line 420 is calculated. In the illustrated embodiments, the goodness metric indicates how well the calibration curve 410 transforms the measured HU values into the property of interest (which is density in the above example). As shown in the figure, the goodness metric varies with respect to the HU values and is the highest in regions where there is no ambiguity between the materials in the histogram 400.

Various techniques may be used to compute values of the goodness metric. In some embodiments, the goodness metric may be calculated from calibration error based on information from the histogram. Also, in some embodiments, the goodness metric may be determined using scaled overlap between the spreads of the different materials.

Here is an example illustrating a specific technique for determining the goodness metric:

Let $N_{i,x}(HU)$ be the number of samples measured from material i, belonging to an interval $[HU-\varepsilon, HU+\varepsilon]$ for some $\varepsilon > 0$.

Then, for a scanning energy x, the goodness metric may be expressed as:

$$q_x(HU) = \frac{\max(\{N_x(HU)\})}{\sum_i N_{i,x}(HU)}$$

where the set $\{N_x(HU)\}$ contains the number of samples belonging to the interval in question from each material. In the above example, $\varepsilon = 0.005$, but other values may be used in other embodiments. In some cases, the optimal value for depends on the distribution of the samples. It should be noted that the technique for determining the goodness metric should not be limited to the above example, and that other techniques may be used to calculate values of the goodness metric.

Referring to FIGS. 4A-4B, one problem illustrated in the above example is the differentiation between materials B and C. They have different densities (0.8 and 1.1), but in the scan, they appear very similar, both having HU values between 1.2 and 1.8. What this means in practice is that the calibration becomes more unstable in this region. For example, the calibration material B has HU value range between about 1.3 and 1.7, and reference density of 0.8. However, the HU values greater than 1.5 may be easily converted into densities around 1.1. In other words, for certain HU values near 1.5, the calibration curve 410 indicates that the corresponding density may be that of material B or material C, and the material identification becomes ambiguous due to the closeness of the peaks and the spreads associated with materials B, C in the histogram 400.

The above problem may be addressed using multi-energy computed tomography (MECT). Even though some materials appear similar (i.e. have similar HU-values) using one scanning energy, switching to another energy may cause them to appear differently, thereby allowing them to be distinguished from each other. This effect is illustrated in FIGS. 5A-5B, where the same calibration process has been carried out with the same materials A, B, C D, with known density values, but using a different energy.

Figure 5A:
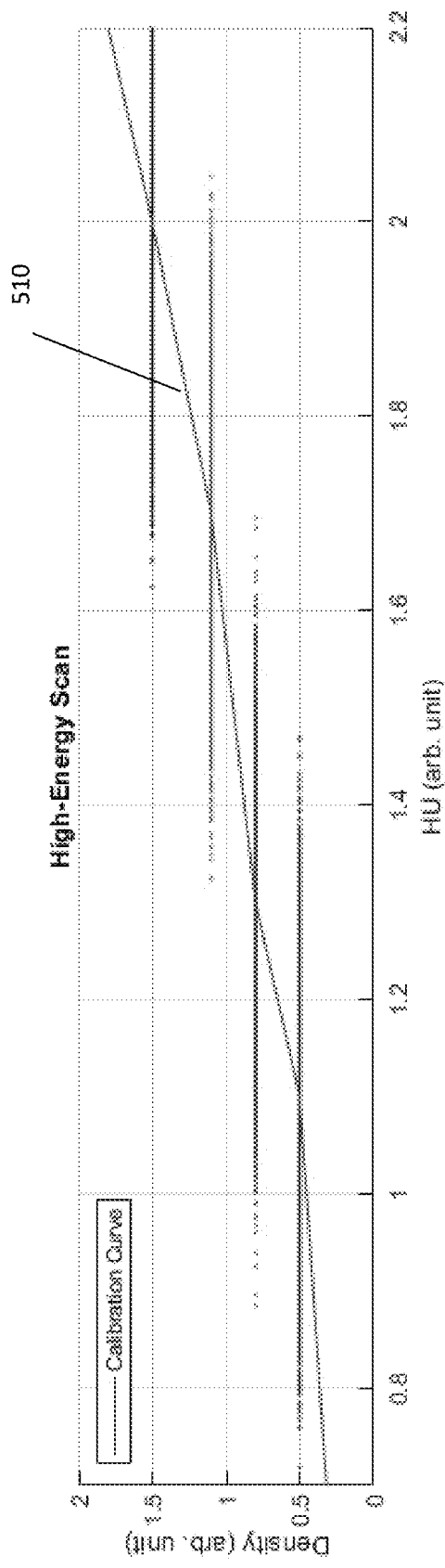
FIG. 5A illustrates a histogram of HU-value spread of several calibration samples obtained using a second energy scan, and a goodness metric calculated from calibration error.

In particular, FIG. 5A illustrates a histogram 500 of HU-value spread of several calibration samples obtained using a second energy scan, and a goodness metric calculated from calibration error. The second energy scan is performed using a second energy that is different from the first energy associated with the first energy scan. In the illustrated example, the histogram 500 is generated using a second energy that is higher than the first energy utilized to perform the scan for the histogram 400. Hereafter, the two scanning energies in FIGS. 4A and 5A will be referred to as "lower" and "upper" energy, or "low" and "high" energy, respectively.

As shown in FIG. 5A, the histogram 500 includes HU-value spreads of four samples (materials)—i.e., spreads 502a-502d for materials A, B, C, D, respectively. The materials A, B, C, D have known respective density values. The histogram 500 is generated using a first energy scan. As shown in the figure, the spread 502a for material A has a peak value when HU value is 1.1, the spread 502b for material B has a peak value when HU value is 1.3, the spread 502c for material C has a peak value when HU value is 1.7, and the spread 502d for material D has a peak value when HU value is 2.0. Accordingly, a calibration curve may be determined based on (HU, density) of the four materials A, B, C, D.

Figure 5B:
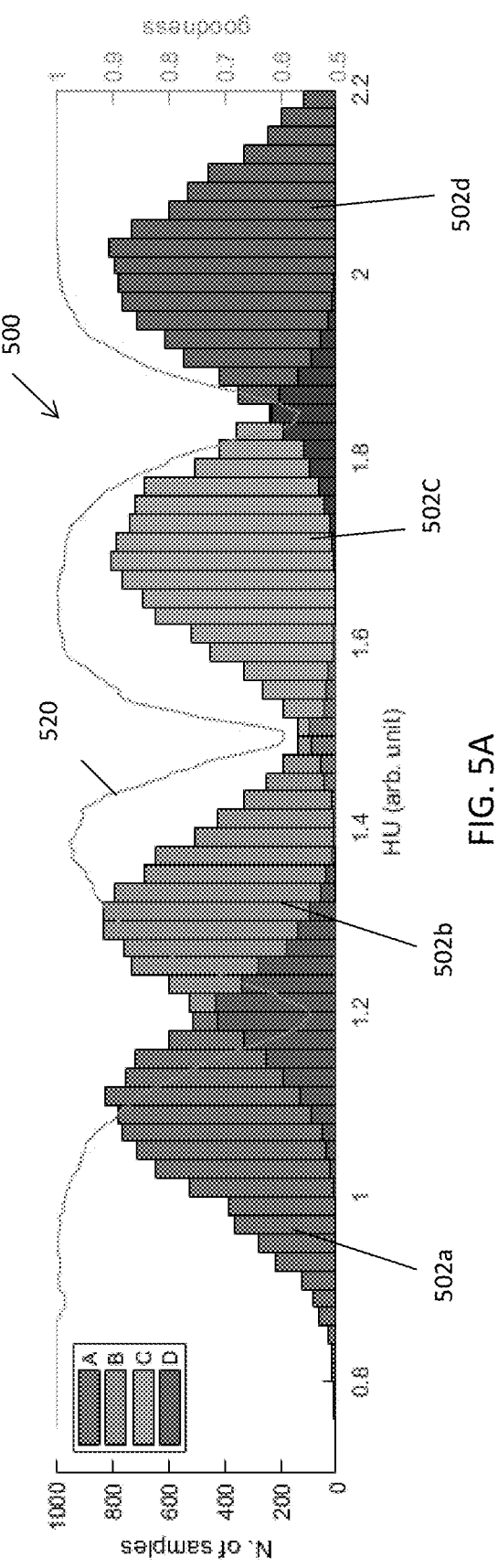
FIG. 5B illustrates a fitted calibration curve for the histogram of FIG. 5A.

FIG. 5B illustrates a fitted calibration curve 510 for the histogram 500 of FIG. 5A generated using the first energy. In particular, material A has known density value of 0.5, and it has a corresponding HU peak at HU=1.1. Material B has known density value of 0.8, and it has a corresponding HU peak at HU=1.3. Material C has known density value of 1.1, and it has a corresponding HU peak at HU=1.7. Material D has known density value of 1.5, and it has a corresponding HU peak at HU=2.0. These four points form part of the calibration curve 410 in FIG. 5B. The calibration curve 510 may be a line fitted to the measurements using any fitting methods, such as the least-squares method. In some embodiments, the calibration curve 510 may be determined as a piecewise linear least-squares fit to the data. In some cases, the calibration curve 510 may include line segments that connect the (HU, density) points for the different materials. The calibration curve 510 may be used to convert measured HU values of a sample into its density based on properties of the calibration materials (e.g., materials A, B, C, D). As shown in the figure, the spreads 502a-502d for the respective materials A, B, C, D are also superimposed onto the calibration curve 510.

As shown in the example of FIGS. 5A-5B, in the upper energy scan, materials A and D appear almost as they did with the lower energy scan, but materials B and C are shifted slightly apart from one another, making it easier to distinguish the two.

As shown in FIG. 5A, a goodness metric represented by line 520 is calculated. In the illustrated embodiments, the goodness metric indicates how well the calibration curve 510 transforms the measured HU values into the property of interest (which is density in the above example). As shown in the figure, the goodness metric varies with respect to HU values, and is the highest in regions where there is no ambiguity between the materials in the histogram 500. The values of the goodness metric may be calculated using the techniques described previously.

Figure 6:
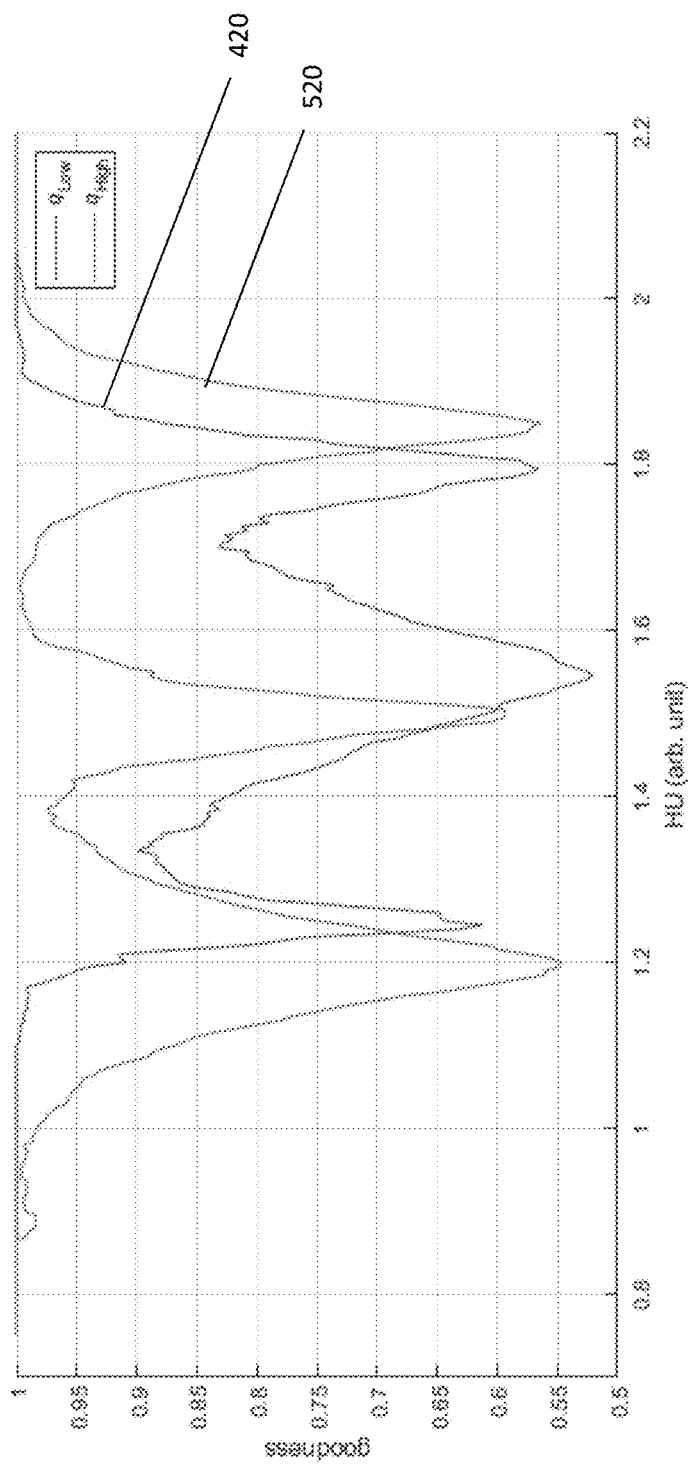
FIG. 6 illustrates the goodness metric of FIG. 4A for the first energy scan, and the goodness metric of FIG. 5A for the second energy scan.

FIG. 6 illustrates the goodness metric 420 of FIG. 4A for the first energy scan, and the goodness metric 520 of FIG. 5A for the second energy scan. In some embodiments, the goodness metrics for the different energy scan (imaging) may be used to calculate a weight for the material property being determined. For example, in some embodiments, a linear weighting function may be used to calculate the weight(s) based on the goodness metrics. One technique for determining weights based on linear weighting is as follows: Let F be the value of the property of interest, $\{HU_x\}$ be the measured HU-values using different energies x, W be the weighting term specific to the energy and HU-values in question, and $f_x$ be the value of the property as read from the energy-specific calibration curve. Then $F(\{HU_x\})=\Sigma_x(W(HU_x)*f_x(HU_x))$, where $\Sigma W=1$. One possible formulation for the weighting term is:

$$W(HU_x) = \frac{q_x(HU_x)}{\Sigma_x(q_x(HU_x))},$$

where $q_x(HU_x)$ is the value of energy-dependent goodness functions (such as those shown in FIG. 6) at point $HU_x$. As an example, assume a dual-energy measurement for an object being examined yielded an HU-value pair $(HU_{Low}, HU_{High})=(1.4, 1.2)$, which locates well inside the HU-ranges of material B according to the histograms 400, 500 of FIGS. 4A and 5A. From the calibration curves 410, 510 of FIGS. 4B and 5B, it can be seen that these correspond to density values 0.74 and 0.65, which are quite far apart. This is because in the high-energy scan the similar appearance between materials A and B skews the result towards lower density values. Accordingly, looking at the goodness values q in FIG. 6, it can be observed that $q_{Low}(1.4) \approx 0.8$ and $q_{high}(1.2) \approx 0.5$, and thus $W_{Low}=0.8/(0.8+0.5)=0.62$ and $W_{High}=0.38$. This gives the weighted density $F=0.62*0.74+0.38*0.65 \approx 0.71$.

Likewise, as a second example, assume another dual-energy measurement pair $(HU_{Low}, HU_{High})=(1.6, 1.4)$. Now the similarity of materials B and C in the low-energy scan skews the densities towards higher values, resulting in density values of 1.1 and 0.88 based on the calibration curves 410, 510 of FIGS. 4B and 5B. From FIG. 6, it can be seen that the goodness values are 0.65 for HU=1.6 in the low energy curve 420, and 0.96 for HU=1.4 in the high energy curve 520. Thus, $W_{LOW}=0.65/(0.65+0.96)=0.4$, and $W_{HIGH}=0.96/(0.65+0.96)=0.6$. The weighted density F is then $0.4*1.1+0.6*0.88=0.97$.

It should be noted that the technique for determining the weight for the material property is not limited to the above example, and that other techniques may be employed in other embodiments. There are multiple different weighting functions (different from the linear one described in the above example) that can be used in other embodiments.

After the weighted density is determined, it may be used to identify the material. In one implementation, database storing density values or density ranges in association with respective material identities may be used to determine an identity of the material based on the weighted density. For example, if material B has established density range [min, max] of [0.6, 1.0], then based on the calculated weighted density of 0.71 in the above first example, it can be determined that the material is material B because 0.71 is within the density range for material B. In some cases, if the weighted density falls within two density ranges for two different materials, then the material may be identified by determining whether the weighted density is closer to an average of a first density range for the first material, or closer to an average of a second density range for the second material. For example, if the calculated weighted density is 0.97 (following the above second example), and if material B has established density range of [0.6, 1.0], and material C has established density range of [0.9, 1.3], then the weighted density 0.97 falls within the ranges for both materials B, C. However, material B has average density of 0.8, and material C has average density of 1.1. Since the weighted density of 0.97 is closer to the average density (1.1) of material C than to that of material B, the material in the object being examined may be identified as material C.

In some embodiments, data values associated with the goodness metric 420 and the goodness metric 520 may be stored in a non-transitory medium, which is accessible later by a processing unit to determine material properties and to identify materials based on the above described technique. In one implementation, the data values of the goodness metric may be stored in a data structure that associates values of the goodness metric with respective HU values. Also, in some embodiments, there may be different data structures for storing the values of the goodness metric in association with HU values for different imaging energies. For example, there may be a first data structure that associates values of goodness metric for a first imaging energy, and a second data structure that associates values of goodness metric for a second imaging energy.

Also, in some embodiments, the weighted property value may be output for presentation to a user in a display, and/or may be stored in a non-transitory medium for later use. Also, in some embodiments, the weighted property value may be used by a treatment planner to perform treatment planning. For example, in some embodiments, the weighted property value may be used to identify object in tissue, and/or for calculation of radiation therapy dose.

In some embodiments, in addition to determining material property for an object being examined, it may be desirable to also determine which material(s) are present in each voxel. This feature may benefit treatment planning and object identification. As the properties of real biological tissues may differ slightly from the materials used for calibration, and as there is some variation between individuals, the calibration data may not be directly used to evaluate which tissue (or combination of different tissue types) a voxel represents. One approach is to first convert the measured HU-values into property values (e.g., density values), and then to compare those to tabulated values. As an example, consider materials A-D with tabulated density ranges listed in the table of FIG. 7. As shown in the figure, the table lists examples of materials A-D and their corresponding density ranges, HU ranges for low energy scan, and HU ranges for high energy scan. Also as shown in the table, there is overlap between some of the materials. In some embodiments, if the density ranges of two materials do not overlap, as is the case with materials C and D, the densities found between the upper boundary of C and lower boundary of D may be considered as a mixture of C and D. Likewise, if the two materials do overlap, the overlapping region is also considered as a mixture. Using this approach, voxels with density higher than 0.9 are deemed to be a mixture of materials B and C, and those with density higher than 1.0 are deemed to be fully material C. However, due to the overlapping of the HU-values of the two materials B, C (See table of FIG. 7), a portion of voxels made of material B may be mistaken as material C, and vice versa (i.e., a portion of voxels made of material C may be mistaken as material B). In this case, the system may apply the above technique of utilizing goodness metric to determine a weighted property value (e.g., weighted density) to obtain a more accurate material differentiation.

However, in some cases, there is also the possibility of two materials sharing the same density, while their other properties (HU-values) are different from one another. To address this, it may be desirable to propagate the material differentiation boundaries to HU-space. This is advantageous because it allows the materials to be differentiated in the HU-space from the get-go without using the calibration curves. FIGS. 8A and 8B illustrate material differentiation in the HU-space for different respective imaging energies.

FIG. 8A shows a graph 800 that includes multiple material fraction lines 810a-810d for different respective materials A-D for a first (e.g., low) imaging energy. Each material fraction line 810 extends in a range of HU values that correspond to those in the second column in the table of FIG. 7. Since the differentiation of the material fraction lines 810a-810d indicate differentiation of the materials A-D, the graph 800 allows a direction identification of material based on its HU value. Using the graph 800, the system can identify a material based on the HU value. For example, if the HU value obtained for an object being examined is 1.4, it can be seen from FIG. 8A that the material is material B (because HU=1.4 is covered by the range of the material fraction line 810b for material B.

As shown in the figure, the material fraction lines 810a-810d for the different respective materials A-D also indicates material fraction values (shown in the vertical axis on the right side of the graph 800) for different HU values. The material fraction values indicate a portion of the material that is present in the object being examined based on HU value. A material fraction value of 1.0 indicates that the part of the object corresponding with the voxel with a certain HU value in the image contains 100% of the corresponding material. Following the above example, if the HU value is 1.4, it can be seen from FIG. 8A that the material is material B (because HU=1.4 is covered by the range of the material fraction line 810b for material B. It can also be seen from FIG. 8A that the material fraction value for HU=1.4 is 1.0, indicating that the material is 100% material B—i.e., it does not contain any material A or material C with material fraction lines 810a, 810c adjacent to the material fraction line 810b for the material B.

Each material fraction line 810 has a horizontal part 812, which corresponds with material fraction value of 1.0, and one or more sloped part(s) 814, 816 corresponding to material fraction values that are less than 1.0. As shown in the figure, the horizontal part 812b of the material fraction line 810b for material B extends from the maximum HU-value of material A (1.33) to the minimum HU-value of material C (1.53). This is the case because the horizontal part 812 for any material should not cover any HU values that also belong to other material(s). Accordingly, if an HU-value is inside the range of only one material, the material fraction is 1 (corresponding to the horizontal part of the material fraction line 810). On the other hand, if the HU-value lies inside the ranges of two materials, then the material fraction line 810 tapers over the overlapping regions to form a sloped part 814/816, like that shown in the graph 800 of FIG. 8A.

One way to construct the graph 800 of FIG. 8A is to use the second column in the table of FIG. 7 to determine the range of the material fraction lines 810a-810d for the respective materials. For example, material A has $HU_{LOW}$ range of 0.6 to 1.33. Accordingly, the material fraction line 810a for material A extends from HU=0.6 to HU=1.33 in the graph 800. Similarly, material e has HU LOW range of 1.17 to 1.57. Accordingly, the material fraction line 810b for material B extends from HU=1.17 to HU=1.57. The same technique is used to determine the range of the material fraction lines 810c, 810d for the materials C, D, respectively. To determine the horizontal part 812 of the material fraction line 810, the second column in the table of FIG. 7 is used to determine the range of HU values that have no overlapping regions. For example, material A has $HU_{LOW}$ values from 0.6 to 1.33, but its adjacent material B has $HU_{LOW}$ values from 1.17 to 1.57. Accordingly, for material A, $HU_{LOW}$ values begin to overlap with those for its adjacent material B at $HU_{LOW}$ value of 1.17. Therefore, the horizontal part 812a of the material fraction line 810a for material A is from $HU_{LOW}$ value of 0.6 to 1.17. From the table of FIG. 7, it can be seen that material A has $HU_{LOW}$ value that overlaps with those for material B until then the end of the $HU_{LOW}$ range (i.e., until value of 1.33) for material A is reached. Thus, the sloped part 816 for the material fraction line 810a of material A extends from $HU_{LOW}$=1.17 (with material fraction value of 1.0) to $HU_{LOW}$=1.33 (with material fraction value of 0 because beyond this point, there is no material A). The sloped parts 814b and 816b for the material fraction line 810b of material B can be determined using the same technique. Similarly, the sloped parts 814c and 816c of the material fraction line 810c of material C, and the sloped part 816d of the material fraction line 810d of material D, can be determined using the same technique.

As shown in FIG. 8A, the sloped parts 812 of adjacent material fraction lines 810 extend across the overlapping HU range, and define material mixing so that the sum of the two materials is always one. Accordingly, the area between the horizontal parts 812 of the material fraction lines 810 for two adjacent materials where neither of the horizontal parts 812 reaches is defined as a mixed-materials area. Each sloped part 812 has a solid portion and a dashed portion. The solid portion of the sloped part 812 indicates that the material is more prominent or dominant (because it corresponds with material fraction values that are higher than 0.5). The dashed portion of the sloped part 812 indicates that the material is less prominent or less dominant (because it corresponds with material fraction values that are below 0.5). It should be noted that the sloped parts 812 of the material fraction lines 810 represent the uncertainty between materials, and correspond with the lower values in the goodness metric shown in FIG. 6.

The material fraction lines 810a-810d in FIG. 8A are generated for a first (e.g., low) imaging energy. Similar material fraction lines can also be generated for other imaging energies. For example, another set of material fraction lines may be generated for a second (e.g., high) imaging energy. FIG. 8B illustrates material fraction lines 860a-860d for different respective materials A-D as function of HU values for a second (e.g., high) imaging energy.

Although only two sets of material fraction lines are shown in FIGS. 8A-8B, in other embodiments, there may be more than two sets of material fraction lines for more than two respective imaging energies. Also, in other embodiments, each graph may have fewer or more than four material fraction lines for fewer or more than four different respective materials. Furthermore, in other embodiments, instead of having a rectilinear configuration for the sloped parts of the material fraction lines, the sloped parts may have other shapes, such as a non-linear shape.

Now, assume a measurement pair of ($HU_{LOW}$=1.4, $HU_{HIGH}$=1.2) for an object being examined is obtained. As discussed in the previous example with reference to FIG. 6, the calculated weights for the two respective imaging energies (based on goodness metric values at these HU values) are 0.62 and 0.38. Looking at the material fraction line 810b for material B in FIG. 8A, it can be seen that the material fraction value is 1.0 for $HU_{LOW}$=1.4. In other words, the lower energy scan suggests the sample to be 100% made of material B for $HU_{LOW}$=1.4. On the other hand, for $HU_{HIGH}$=1.2, from the material fraction lines 860a and 860b in FIG. 8B, it can be seen that the material fraction value is 0.5 for material B and 0.5 for material A. In some embodiments, a metric (portion metric) may be calculated using the determined material fraction values. In one implementation, the portion metric PM may be computed as a sum of weight*material fraction value. Following the above example, the portion metric PM for the object being examined is PM=W1*MF1+W2*MF2=0.62*100%+0.38*50%=81% (i.e., 81% of the material is material B).

As another example, consider another measurement pair of ($HU_{LOW}$=1.55, $HU_{HIGH}$=1.5) for an object being examined is obtained. In such cases, as shown in FIGS. 8A-8B, both high- and low-energy fractions would point towards a 50-50 distribution of materials B and C. Also, from FIG. 6, it can be seen that the respective goodness values are 0.53 and 0.61 for ($HU_{LOW}$=1.55, $HU_{HIGH}$=1.5). The weight for low energy is then 0.53/(0.53+0.61)=0.46, and the weight for high energy is then 0.61/(0.53+0.61)=0.54. The portion metric PM for material B is then 0.46*50%+0.54*50%=50% (i.e., 50% of the material is material B). This means that equal distribution of materials B and C is probable.

In some embodiments, the portion metric may be output for presentation to a user in a display, and/or may be stored in a non-transitory medium for later use. Also, in some embodiments, the portion metric may be used by a treatment planner to perform treatment planning. For example, in some embodiments, the portion metric may be used to identify object in tissue, and/or for calculation of radiation therapy dose.

It should be noted that the boundary values of low energy and high energy in the table of FIG. 7 do not necessarily exactly match the values in FIGS. 4-5. Similarly, because the graphs in FIG. 8 are based on the values in FIG. 7, features of the graphs in FIG. 8 may also not identically align with FIGS. 4-5 (and similarly FIG. 6, which is derived from FIGS. 4-5). In an ideal world, the boundary values in FIG. 7 would match those in FIGS. 4 and 5, and the features of the graphs in FIG. 8 would match those in FIGS. 4-6. However, in reality, there will be some inaccuracies in converting densities to HU values, as well as distortion and instabilities in calibration that will contribute to the mismatch. That is why the low-energy scan and the high-energy scan may have material boundaries that are distorted. Various techniques may be employed to distinguish the material in question while considering these distorted boundaries. In some embodiments, a higher weight may be applied to the non-distorted boundaries using the goodness-metric to address the distortion.

In other embodiments, FIGS. 4-8 may be considered as separate respective numerical examples that do not necessarily relate to each other.

Figure 9:
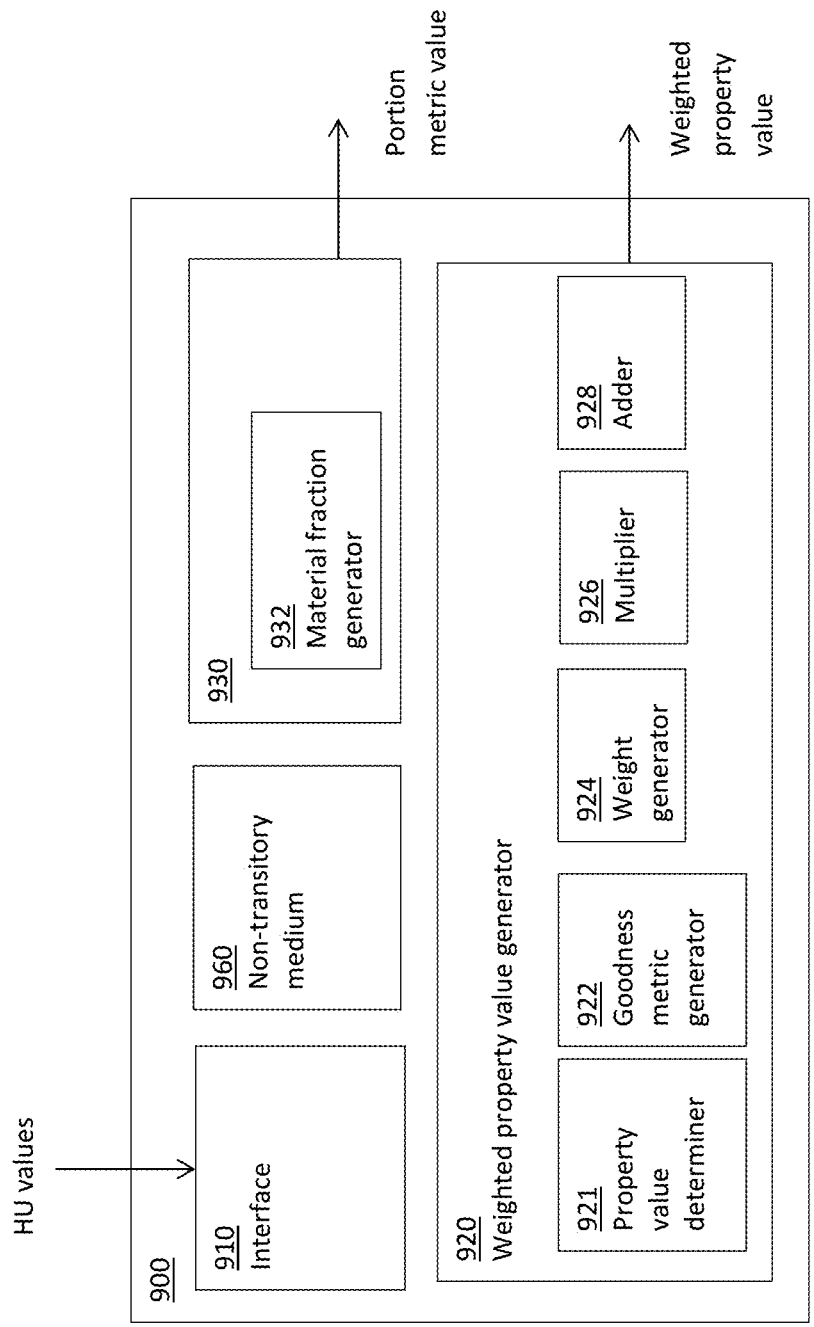
FIG. 9 illustrates a processing unit in accordance with some embodiments.

In some embodiments, the above calculation and determination of the various parameters (e.g., property values, goodness metric values, weights, weighted property value, material fraction values, portion metric, etc.) may be performed by a processing unit. FIG. 9 illustrates a processing unit 900 configured to provide one or more features described herein in accordance with some embodiments. As shown in the figure, the processing unit 900 includes an interface 910 configured to obtain a first HU value associated with a first image of an object being examined, and to obtain a second HU value associated with a second image of the object. The first image may be created using a first energy having a first energy level, and the second image may be created using a second energy having a second energy level that is different from the first energy level. Each of the first image and the second image may be a CT image, a x-ray image, or any of other type of image.

The processing unit 900 also includes a weighted property value generator 920 configured to determine a weighted property value for the object based at least in part on the first HU value and the second HU value. In some embodiments, the weighted property value may be a weighted density for the object. In other embodiments, the weighted property value may be weighted proton stopping power, weighted electron density, etc.

Also, in some embodiments, the weighted property value generator 920 may be configured to determine the weighted density based on weights calculated using at least a first (e.g., low) energy metric value and a second (e.g., high) energy metric value. The first energy metric value indicates how well the first HU value correlates with a first property identification, and the second energy metric value indicates how well the second HU value correlates with a second property identification. As an example, the first energy metric value may be a value of the goodness metric described with reference to FIG. 4A and FIG. 6, and the second energy metric value may be a value of the goodness metric described with reference to FIG. 5A and FIG. 6. Thus, in some embodiments, the first energy metric may be a goodness metric calculated from calibration error for histogram of HU-value spread of a calibration sample using first (e.g., low) energy. Similarly, the second energy metric may be a goodness metric calculated from calibration error for histogram of HU-value spread of a calibration sample using second (e.g., high) energy.

As shown in FIG. 9 the weighted property value generator 920 includes a property value determiner 921. The property value determiner 921 is configured to determine property values for the object being examined for different respective imaging energies based on HU values. In some embodiments, the property value determiner 921 is configured to access a non-transitory medium storing calibration curves or associated data like those described with reference to FIGS. 4B and 5B for different respective imaging energies. Based on the HU values from the imaging performed on the object at different respective energies, the property value determiner 921 then utilizes the stored calibration curves or its associated data to determine the respective property values for the corresponding HU values. As discussed with reference to FIGS. 4A-5B, for a given HU value obtained from imaging of the object, a corresponding property value (e.g., density value) may be determined from the calibration curve 410/510, which provides a relationship between HU values and property values. This determination of property value is performed by the property value determiner 921 based on the relationship between the HU values and the property values for each of a plurality of imaging energies.

In some embodiments, the processing unit 900 is configured to determine an identity of the object based on the property values determined by the property value determiner 921, and/or based on histogram information, for the respective different imaging energies. For example, if a dual-energy measurement for an object being examined yielded an HU-value pair $(HU_{Low}, HU_{High})=(1.4, 1.2)$, it can be seen that this data locates well inside the HU-ranges of material B according to the histograms 400, 500 of FIGS. 4A and 5A.

As shown in FIG. 9, the weighted property value generator 920 also includes a goodness metric generator 922 configured to determine a first (e.g., low) energy metric value and a second (e.g., high) energy metric value. In one implementation, the first and second energy metric values are goodness metric values for respective imaging energies. In such cases, the goodness metric generator 922 is configured to access goodness metric values stored in a non-transitory medium to determine the goodness metric values. The goodness metric generator 922 may perform table lookup to determine goodness metric values based on HU values associated with different respective imaging energies. In some cases, the goodness metric generator 922 may also perform interpolation if a HU value for the object being examined falls between two HU values stored in the medium. In such cases, the goodness metric generator 922 may determine the goodness metric based on an interpolation between two goodness metric values stored in the medium that correspond with the two stored HU values.

The weighted property value generator 920 also includes a weight generator 924 configured to generate respective weights for different imaging energies based on the metric values (e.g., goodness metric values) determined by the goodness metric generator 922. For example, if the goodness metric generator 922 provides N metric values $M_1$-$M_N$, then the weight generator 924 generates N respective weights $W_1$-$W_N$ based on the equation: $W_n=M_n/(Sum (M_1$-$M_N))$, for n=1 to N.

The weighted property value generator 920 further includes a multiplier 926 and an adder 928 configured to determine a weighted property value for the object being examined based on the weights determined by the weight generator 924. In the illustrated embodiments, the multiplier 926 is configured to multiply each weight by the respective property value determined by the property value determiner 921 for the respective imaging energy. For example, if there are three weights W1, W2, W3 for the respective imaging energies E1, E2, E3, and if there are three property values P1, P2, P3 for the respective imaging energies E1, E2, E3 determined by the property value determiner 921, then the multiplier 926 multiplies W1 by P1, multiplies W2 by P2, and multiplies W3 by P3 (i.e., determines W1*P1, W2*P2, W3*P3). The adder 928 is configured to add the terms (e.g., W1*P1, W2*P2, etc.) output by the multiplier 926 to obtain a weighted property value for the object being examined.

In the illustrated embodiments, the processing unit 900 also includes a portion metric generator 930 configured to determine a metric indicating a percentage or an amount of an identified material in the object. The portion metric generator 930 includes a material fraction generator 932 configured to determine material fraction values for different respective imaging energies based on HU values for the different respective imaging energies. For example, if an object is being scanned with two imaging energies, then the material fraction generator 932 is configured to determine a first material fraction based on the first HU value for the first imaging energy, and a second material fraction based on the second HU value for the second imaging energy. The material fraction generator 930 may access a non-transitory medium storing information like those in FIGS. 8A and 8B to determine material fractions for respective imaging energies. For example, in some embodiments, the non-transitory medium may store material fraction values as a function of HU values, or storing parameter(s) of function(s) associating the material fraction values with HU values.

The portion metric generator 930 is configured to compute a metric (e.g., a portion metric) for the object based on the material fractions determined by the material fraction generator 932. In some embodiments, the portion metric generator 930 of the processing unit is configured to compute the metric (e.g., portion metric) for the object based on the first material fraction and the second material fraction, and also based on a first weight and a second weight. In the illustrated embodiments, the portion metric is based on the first weight times the first material fraction and the second weight times the second material fraction. In general, for N imaging energies, the portion metric PM may be computed by the portion metric generator 930 as PM=sum ($MF_n * W_n$) for n=1 to N, wherein $MF_n$ is material fractions for the different respective imaging energies, and $W_n$ are the weights for the different respective imaging energies.

In some embodiments, the weights $W_n$ may be those generated by the weight generator 924. In such cases, the weights for determining the weighted property value by the weighted property value generator 920 may also be utilized by the portion metric generator 930 to determine the portion metric for the object being examined. In other embodiments, the weights for calculating the portion metric may be different from the weights for calculating the weighted property value generator.

As shown in FIG. 9, the processing unit 900 may also include a non-transitory medium 960. In the illustrated embodiments, the non-transitory medium 960 stores information that can be used by the processing unit 900 to determine material properties, and metrics. By means of non-limiting examples, the information stored in the non-transitory medium 960 may be: histogram information (such as the HU-value spreads for different materials, HU-values corresponding to respective peaks for different materials, etc.), calibration curve information (such as fitted curve or line, parameter(s) for such fitted curve or line, data points defining such fitted curve or line (e.g., [peak HU value, density value] data point), etc.), metric values and/or functions for different imaging energies (such as goodness metric values and/or functions, like those shown in FIG. 6), or any combination of the foregoing. Also, in some embodiments, the non-transitory medium 960 may store density ranges, $HU_{LOW}$ range, and $HU_{HIGH}$ range for different respective materials (like the example of values shown in FIG. 7). Furthermore, in some embodiments, the non-transitory medium 960 may store material fraction information for different materials with respect to different HU values for different energies (like the examples shown in FIGS. 8A-8B).

In some embodiments, the processing unit 900 may be a part of the processing unit 54 of FIG. 3, or may be communicatively coupled to the processing unit 54 of FIG. 3. In other embodiments, the processing unit 900 may be a part of a workstation, such as a computer or a handheld device (e.g., cell phone, tablet, etc.). The processing unit 900 may be implemented using hardware, software, or a combination of both. In some embodiments, the hardware may include one or more processing circuit, such as one or more processor(s). Furthermore, in some embodiments, the processing unit 900 may be a part of an imaging device, such as that in a medical device (e.g., a medical diagnostic system), or that in an object scanner. The imaging device may configured to generate the first image using first imaging energy (e.g., low energy), and the second image using second imaging energy (e.g., high energy).

Figure 10:
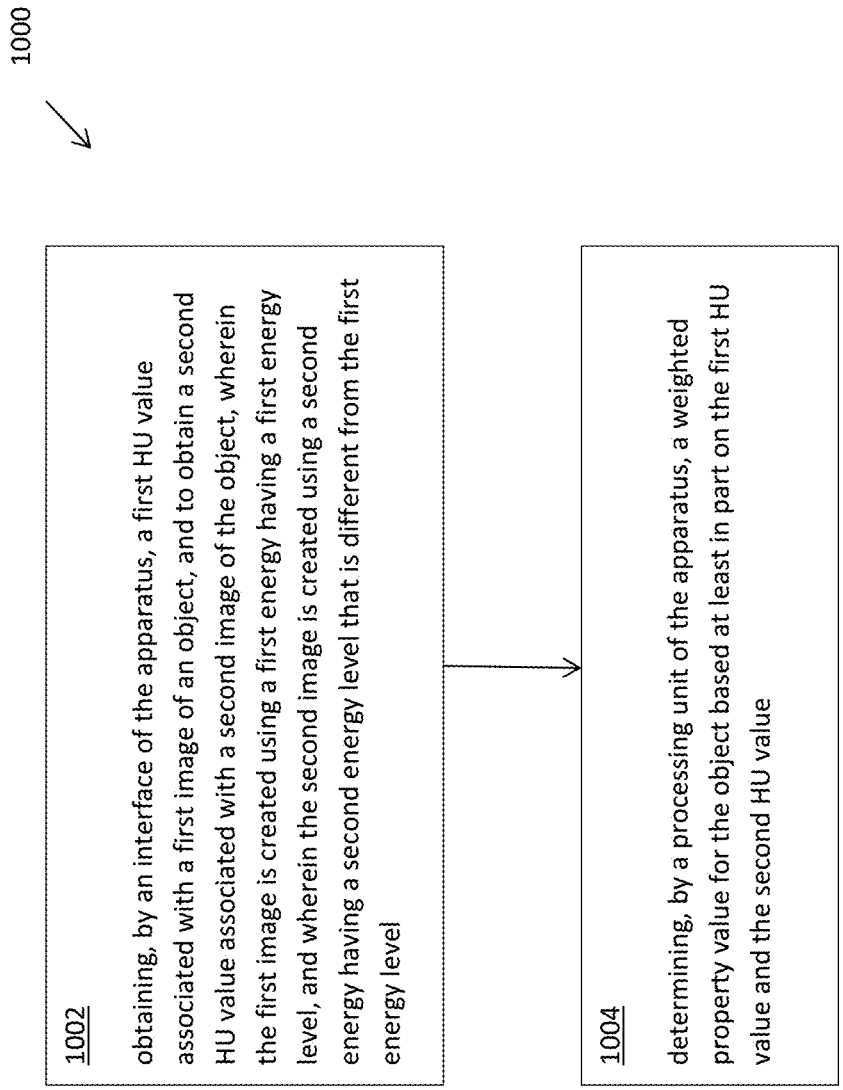
FIG. 10 illustrates a method in accordance with some embodiments.

FIG. 10 illustrates a method 1000 in accordance with some embodiments. The method 1000 may be performed by the apparatus of FIG. 3 in some embodiments. As shown in FIG. 10, the method 1000 includes: obtaining, by an interface of the apparatus, a first HU value associated with a first image of an object, and to obtain a second HU value associated with a second image of the object, wherein the first image is created using a first energy having a first energy level, and wherein the second image is created using a second energy having a second energy level that is different from the first energy level (item 1002). The method 1000 also includes: determining, by a processing unit of the apparatus, a weighted property value for the object based at least in part on the first HU value and the second HU value (item 1004).

Optionally, in the method 1000, the weighted property value comprises a weighted density for the object.

Optionally, in the method 1000, the weighted density is based on weights calculated using a low energy metric value and a high energy metric value.

Optionally, in the method 1000, the low energy metric value indicates how well the first HU value correlates with a first property identification, and the high energy metric value indicates how well the second HU value correlates with a second property identification.

Optionally, in the method 1000, the weights comprise a first weight and a second weight; wherein the first weight is calculated as the low energy metric value/(the low energy metric value plus the high energy metric value); and wherein the second weight is calculated as the high energy metric value/(the low energy metric value plus the high energy metric value).

Optionally, in the method 1000, the low energy metric is a goodness metric calculated from calibration error for histogram of HU-value spread of a calibration sample.

Optionally, the method 1000 further includes comprising determining, by the processing unit, an identity of the object based on the weighted property value.

Optionally, the method 1000 further includes determining, by the processing unit, a first material fraction based on the first HU value, and a second material fraction based on the second HU value; and computing, by the processing unit, a metric for the object based on the first material fraction and the second material fraction.

Optionally, the metric indicates a percentage or an amount of an identified material in the object.

Optionally, the first material fraction is determined by the processing unit accessing a non-transitory medium storing material fraction values as a function of HU values, or storing parameter(s) of function(s) associating the material fraction values with HU values.

Optionally, the metric for the object is computed based on the first material fraction and the second material fraction, and also based on a first weight and a second weight.

Optionally, the metric is based on the first weight times the first material fraction and the second weight times the second material fraction.

Optionally, the first weight and the second weight are based on a low energy metric value and a high energy metric value.

Optionally, the first weight is calculated as the low energy metric value/(the low energy metric value plus the high energy metric value); and wherein the second weight is calculated as the high energy metric value/(the low energy metric value plus the high energy metric value).

Optionally, the low energy metric is a goodness metric calculated from calibration error for histogram of HU-value spread of a calibration sample.

Optionally, each of the first image and the second image comprises a CT image or a x-ray image.

Optionally, the method further includes generating the first image and the second image by an imaging device, wherein the imaging device is a part of a medical device or a part of an object scanner.

Specialized Processing System

Figure 11:
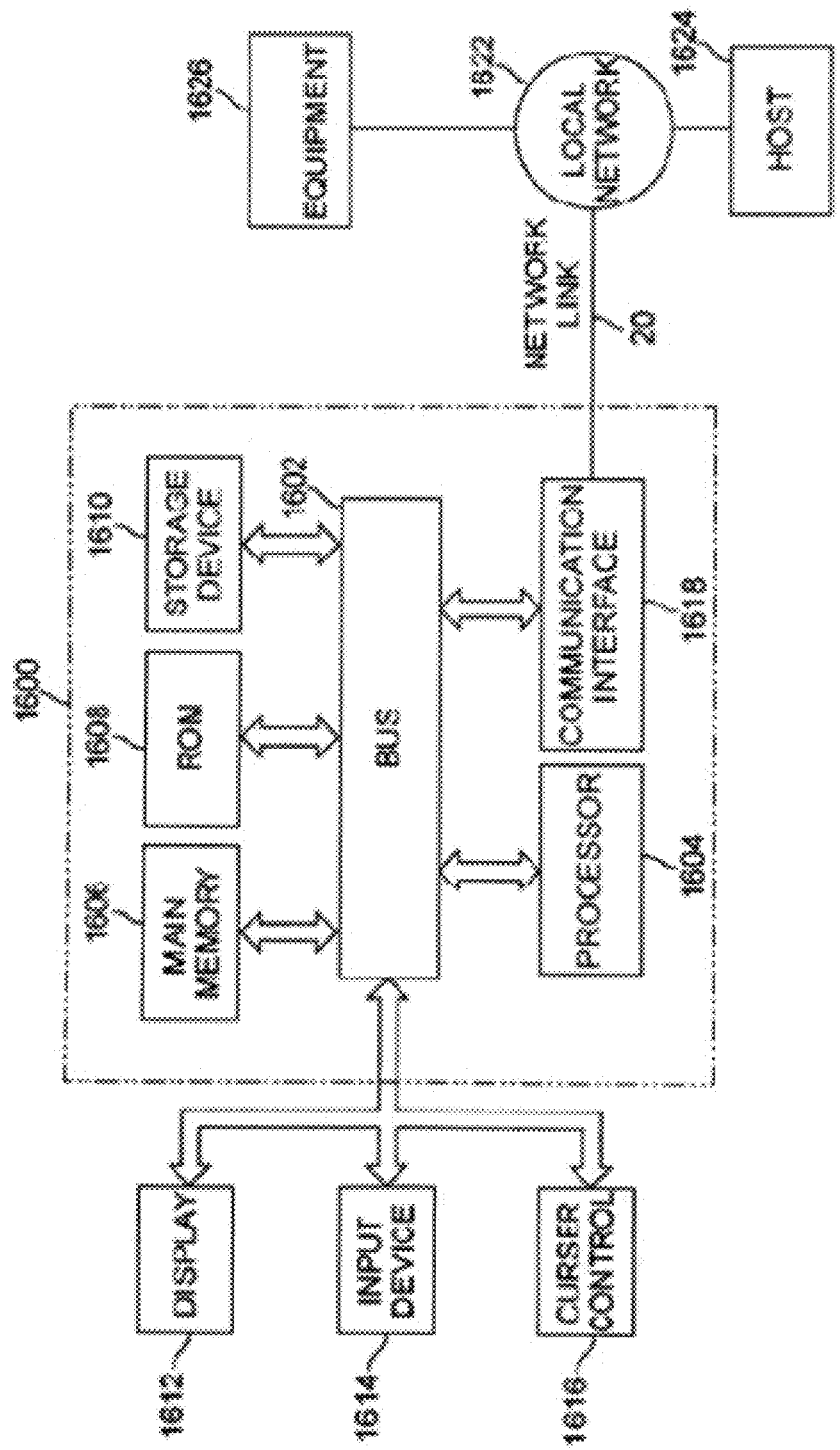
FIG. 11 illustrates a specialized processing system in accordance with some embodiments.

FIG. 11 is a block diagram illustrating an embodiment of a specialized processing system 1600 that can be used to implement various features described herein. For example, in some embodiments, the processing system 1600 may be used to implement the processing unit 900 of FIG. 9. In addition, in some embodiments, the processing system 1600 may be configured to perform the method of FIG. 10. Furthermore, in some embodiments, the processing system 1600 may be used to implement the processing unit 54 of FIG. 3. The processing system 1600 may also be used to implement a control that controls an operation of the imager 100, and/or a control that controls an operation of the radiation system 10.

As shown in FIG. 11, the processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk, solid state disk, or optical disk, is provided and coupled to the bus 1602 for storing information and instructions.

The processor system 1600 may be coupled via the bus 1602 to a display 167, such as a flat screen monitor, for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical, solid state or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a flexible disk, hard disk, magnetic tape, or any other magnetic medium, a CD-ROM, any other optical medium, any other physical medium with patterns of holes, a RAM, a PROM, and EPROM, a FLASH-EPROM, solid state disks any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk or solid state disk of a remote computer. The remote computer can load the instructions into its dynamic memory and send the instructions over a network, such as the Internet. The processing system 1600 can receive the data on a network line. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source and/or an imaging device or a switch operatively coupled to a radiation beam source and/or an imaging device. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

As used in this specification, terms such as "first", "second", etc., are used to identify different items, and do not necessarily refer to the order of items.

Also, as used in this specification, the term "image" may refer to a displayed image and/or to an image that is in electronic form that is not displayed.

Exemplary imaging acquisition apparatuses and methods are set out in the following items:

Item 1: An apparatus for determining material property, includes: an interface configured to obtain a first HU value associated with a first image of an object, and to obtain a second HU value associated with a second image of the object, wherein the first image is created using a first energy having a first energy level, and wherein the second image is created using a second energy having a second energy level that is different from the first energy level; and a processing unit configured to determine a weighted property value for the object based at least in part on the first HU value and the second HU value.

Item 2: In the apparatus, the weighted property value comprises a weighted density for the object.

Item 3: The weighted density is based on N weights calculated using N metric values for N respective imaging energies.

Item 4: The N metric values comprises a first metric value indicates how well the first HU value correlates with a first property identification, and a second metric value indicates how well the second HU value correlates with a second property identification.

Item 5: The N metric values are $M_1$-$M_N$, and the N weights are $W_1$-$W_N$ calculated as $W_n = M_n/(\text{Sum }(M_1 - M_N))$, for n=1 to N.

Item 6: At least one of the N metric values is a goodness metric calculated from calibration error for histogram of HU-value spread of a calibration sample.

Item 7: In the apparatus, the processing unit is configured to determine an identity of the object based on the weighted property value.

Item 8: In the apparatus, the processing unit is also configured to determine a first material fraction based on the first HU value, and a second material fraction based on the second HU value; and wherein the processing unit is configured to compute a metric for the object based on the first material fraction and the second material fraction.

Item 9: In the apparatus, the metric indicates a percentage or an amount of an identified material in the object.

Item 10: In the apparatus, the processing unit is configured to determine the first material fraction by accessing a non-transitory medium storing material fraction values as a function of HU values, or storing parameter(s) of function(s) associating the material fraction values with HU values.

Item 11: The apparatus further includes the non-transitory medium.

Item 12: In the apparatus, the processing unit is configured to compute the metric for the object based on the first material fraction and the second material fraction, and also based on a first weight and a second weight.

Item 13: In the apparatus, the metric is based on the first weight times the first material fraction and the second weight times the second material fraction.

Item 14: In the apparatus, each of the first weight and the second weight is based at least on a first metric value and a second metric value.

Item 15: In the apparatus, the first weight is calculated as the first metric value divided by a sum of metric values that includes the first metric value and the second metric value; and wherein the second weight is calculated as the second metric value divided by the sum of metric values that includes the first metric value and the second metric value.

Item 16: In the apparatus, the first metric value is a goodness metric calculated from calibration error for histogram of HU-value spread of a calibration sample.

Item 17: In the apparatus, each of the first image and the second image comprises a CT image or a x-ray image.

Item 18: The apparatus further includes an imaging device configured to generate the first image and the second image, wherein the imaging device is a part of a medical device or a part of an object scanner.

Item 19: A method performed by an apparatus, includes: obtaining, by an interface of the apparatus, a first HU value associated with a first image of an object, and to obtain a second HU value associated with a second image of the object, wherein the first image is created using a first energy having a first energy level, and wherein the second image is created using a second energy having a second energy level that is different from the first energy level; and determining, by a processing unit of the apparatus, a weighted property value for the object based at least in part on the first HU value and the second HU value.

Item 20: In the method, the weighted property value comprises a weighted density for the object.

Item 21: In the method, the weighted density is based on N weights calculated using N metric values for N respective imaging energies.

Item 22: In the method, the N metric values comprises a first metric value indicates how well the first HU value correlates with a first property identification, and a second metric value indicates how well the second HU value correlates with a second property identification.

Item 23: In the method, the N metric values are $M_1$-$M_N$, and the N weights are $W_1$-$W_N$ calculated as $W_n = M_n/(\text{Sum }(M_1 - M_N))$, for n=1 to N.

Item 24: In the method, at least one of the N metric values is a goodness metric calculated from calibration error for histogram of HU-value spread of a calibration sample.

Item 25: The method further includes comprising determining, by the processing unit, an identity of the object based on the weighted property value.

Item 26: The method further includes determining, by the processing unit, a first material fraction based on the first HU value, and a second material fraction based on the second HU value; and computing, by the processing unit, a metric for the object based on the first material fraction and the second material fraction.

Item 27: In the method, the metric indicates a percentage or an amount of an identified material in the object.

Item 28: In the method, the first material fraction is determined by the processing unit accessing a non-transitory medium storing material fraction values as a function of HU values, or storing parameter(s) of function(s) associating the material fraction values with HU values.

Item 29: In the method, the metric for the object is computed based on the first material fraction and the second material fraction, and also based on a first weight and a second weight.

Item 30: In the method, the metric is based on the first weight times the first material fraction and the second weight times the second material fraction.

Item 31: In the method, each of the first weight and the second weight is based at least on a first metric value and a second metric value.

Item 32: In the method, the first weight is calculated as the first metric value divided by a sum of metric values that includes the first metric value and the second metric value; and wherein the second weight is calculated as the second metric value divided by the sum of metric values that includes the first metric value and the second metric value.

Item 33: In the method, the first metric value is a goodness metric calculated from calibration error for histogram of HU-value spread of a calibration sample.

Item 34: In the method, each of the first image and the second image comprises a CT image or a x-ray image.

Item 35: The method further includes generating the first image and the second image by an imaging device, wherein the imaging device is a part of a medical device or a part of an object scanner.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An apparatus for determining material property, comprising:
an interface configured to obtain a first HU value associated with a first image of an object, and to obtain a second HU value associated with a second image of the object, wherein the first image is created using a first energy having a first energy level, and wherein the second image is created using a second energy having a second energy level that is different from the first energy level; and
a processing unit configured to determine a weighted property value for the object based at least in part on the first HU value and the second HU value;
wherein the weighted property value comprises a weighted density for the object.

2. The apparatus of claim 1, wherein the weighted density is based on N weights calculated using N metric values for N respective imaging energies.

3. The apparatus of claim 2, wherein the N metric values comprises a first metric value that indicates how well the first HU value correlates with a first property identification, and a second metric value that indicates how well the second HU value correlates with a second property identification.

4. The apparatus of claim 2, wherein the N metric values are $M_1$-$M_N$, and the N weights are $W_1$-$W_N$ calculated as $W_n = M_n/(\text{Sum } (M_1\text{-}M_N))$, for n=1 to N.

5. The apparatus of claim 2, wherein at least one of the N metric values is a goodness metric calculated from calibration error for histogram of HU-value spread of a calibration sample.

6. The apparatus of claim 1, wherein the processing unit is configured to determine an identity of the object based on the weighted property value.

7. The apparatus of claim 3, wherein each of the first image and the second image comprises a CT image or a x-ray image.

8. The apparatus of claim 1, further comprising an imaging device configured to generate the first image and the second image, wherein the imaging device is a part of a medical device or a part of an object scanner.

9. An apparatus for determining material property, comprising:
an interface configured to obtain a first HU value associated with a first image of an object, and to obtain a second HU value associated with a second image of the object, wherein the first image is created using a first energy having a first energy level, and wherein the second image is created using a second energy having a second energy level that is different from the first energy level; and
a processing unit configured to determine a weighted property value for the object based at least in part on the first HU value and the second HU value;
wherein the processing unit is also configured to determine a first material fraction based on the first HU value, and a second material fraction based on the second HU value; and
wherein the processing unit is configured to compute a metric for the object based on the first material fraction and the second material fraction.

10. The apparatus of claim 9, wherein the metric indicates a percentage or an amount of an identified material in the object.

11. The apparatus of claim 9, wherein the processing unit is configured to determine the first material fraction by accessing a non-transitory medium storing material fraction values as a function of HU values, or storing parameter(s) of function(s) associating the material fraction values with HU values.

12. The apparatus of claim 9, wherein the processing unit is configured to compute the metric for the object based on the first material fraction and the second material fraction, and also based on a first weight and a second weight.

13. The apparatus of claim 12, wherein the metric is based on the first weight times the first material fraction and the second weight times the second material fraction.

14. The apparatus of claim 12, wherein each of the first weight and the second weight is based at least on a first metric value and a second metric value.

15. The apparatus of claim 14, wherein the first weight is calculated as the first metric value divided by a sum of metric values that includes the first metric value and the second metric value; and
wherein the second weight is calculated as the second metric value divided by the sum of metric values that includes the first metric value and the second metric value.

16. The apparatus of claim 14, wherein the first metric value is a goodness metric calculated from calibration error for histogram of HU-value spread of a calibration sample.

17. A method performed by an apparatus, comprising:
obtaining, by an interface of the apparatus, a first HU value associated with a first image of an object, and to obtain a second HU value associated with a second image of the object, wherein the first image is created using a first energy having a first energy level, and wherein the second image is created using a second energy having a second energy level that is different from the first energy level;
determining, by a processing unit of the apparatus, a weighted property value for the object based at least in part on the first HU value and the second HU value;
determining, by the processing unit, a first material fraction based on the first HU value, and a second material fraction based on the second HU value; and
computing, by the processing unit, a metric for the object based on the first material fraction and the second material fraction.

* * * * *